(12) United States Patent
Kappus et al.

(10) Patent No.: US 10,772,642 B2
(45) Date of Patent: Sep. 15, 2020

(54) SURGICAL FORCEPS

(71) Applicant: COVIDIEN LP, Mansfield, MA (US)

(72) Inventors: John J. Kappus, Denver, CO (US); David N. Heard, Boulder, CO (US); Joe D. Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 396 days.

(21) Appl. No.: 15/672,383

(22) Filed: Aug. 9, 2017

(65) Prior Publication Data

US 2018/0049752 A1 Feb. 22, 2018

Related U.S. Application Data

(60) Provisional application No. 62/376,434, filed on Aug. 18, 2016.

(51) Int. Cl.
*A61B 17/00* (2006.01)
*A61B 17/16* (2006.01)
(Continued)

(52) U.S. Cl.
CPC .......... *A61B 17/1611* (2013.01); *A61B 17/29* (2013.01); *A61B 17/295* (2013.01);
(Continued)

(58) Field of Classification Search
CPC ..... A61B 17/28; A61B 17/29; A61B 17/1606; A61B 17/07207; A61B 17/320016;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Heniford et al. "Initial Research and Clinical Results with an Electrothermal Bipolar Vessel Sealer" Oct. 1999.
(Continued)

*Primary Examiner* — Andrew M Tecco
*Assistant Examiner* — Eyamindae C Jallow
(74) *Attorney, Agent, or Firm* — Carter, DeLuca & Farrell LLP

(57) ABSTRACT

A surgical instrument includes a housing, an elongated shaft extending distally from the housing, an end effector assembly, and a trigger assembly. The trigger assembly is disposed in mechanical cooperation with the housing and is configured to longitudinally translate a drive member. The trigger assembly includes a trigger, a gear assembly, a spool, a slider, and a flexible drive member. The trigger is disposed in mechanical cooperation with the gear assembly. The flexible drive member is configured to engage the gear assembly, the spool, and the slider. Movement of the trigger with respect to the housing results in movement of the flexible drive member with respect to the housing and longitudinal movement of the slider with respect to the housing.

19 Claims, 18 Drawing Sheets

(51) Int. Cl.
*A61B 17/29* (2006.01)
*A61B 17/32* (2006.01)
*A61B 17/295* (2006.01)
*A61B 18/14* (2006.01)
*A61B 17/3201* (2006.01)
*A61B 34/30* (2016.01)
*A61B 90/00* (2016.01)

(52) U.S. Cl.
CPC .. *A61B 17/320016* (2013.01); *A61B 18/1445* (2013.01); *A61B 17/3201* (2013.01); *A61B 34/30* (2016.02); *A61B 90/03* (2016.02); *A61B 2017/00353* (2013.01); *A61B 2017/2913* (2013.01); *A61B 2017/2915* (2013.01); *A61B 2017/2923* (2013.01); *A61B 2018/1452* (2013.01)

(58) Field of Classification Search
CPC .. A61B 2017/00353; A61B 2017/2923; A61B 2017/2943
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,582,615 A * | 12/1996 | Foshee | A61B 17/2909 606/139 |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 9,566,065 B2 * | 2/2017 | Knodel | A61B 17/068 |
| 2005/0209596 A1 | 9/2005 | Daniels et al. | |
| 2007/0175964 A1 * | 8/2007 | Shelton, IV | A61B 17/072 227/180.1 |
| 2010/0004677 A1 | 1/2010 | Brostoff et al. | |
| 2011/0276049 A1 * | 11/2011 | Gerhardt | A61B 18/1402 606/45 |
| 2012/0316601 A1 | 12/2012 | Twomey | |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0332578 A1 * | 11/2014 | Fernandez | A61B 17/068 227/175.1 |
| 2014/0336635 A1 | 11/2014 | Hart et al. | |
| 2014/0339286 A1 * | 11/2014 | Motooka | A61B 17/07207 227/175.2 |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |
| 2015/0209059 A1 * | 7/2015 | Trees | A61B 18/1445 606/170 |
| 2016/0135869 A1 * | 5/2016 | Jadhav | F16H 19/06 606/52 |
| 2017/0143361 A1 * | 5/2017 | Boudreaux | A61B 17/29 |
| 2017/0143362 A1 * | 5/2017 | Cagle | A61B 18/1445 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 4211417 A1 | 10/1993 |
| DE | 04303882 C2 | 2/1995 |

(56) References Cited

FOREIGN PATENT DOCUMENTS

| | | |
|---|---|---|
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009318 U1 | 8/2007 |
| DE | 202007009317 U1 | 10/2007 |
| DE | 202007016233 U1 | 1/2008 |
| DE | 102008018406 B3 | 7/2009 |
| EP | 0589453 A2 | 3/1994 |
| EP | 1159926 A2 | 12/2001 |
| EP | 1281878 A1 | 2/2003 |
| EP | 2777586 A1 | 9/2014 |
| EP | 2890309 A1 | 7/2015 |
| JP | 61-501068 | 9/1984 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 3/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 910223 | 1/1997 |
| JP | 09000538 A | 1/1997 |
| JP | 9-122138 A | 5/1997 |
| JP | 1024051 | 1/1998 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-029355 A | 2/2001 |
| JP | 2001029356 A | 2/2001 |
| JP | 2001128990 A | 5/2001 |
| JP | 2001-190564 A | 7/2001 |
| JP | 2001-003400 | 11/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Extended European Search Report for EP 16196110 dated Dec. 23, 2016.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemontoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/ Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970; filed Dec. 17, 2008; inventor: Paul R. Sremcich, abandoned.
U.S. Appl. No. 14/065,644, filed Oct. 29, 2013; inventor: Reschke, abandoned.

\* cited by examiner

SURGICAL FORCEPS

CROSS REFERENCE TO RELATED APPLICATION

The present application claims the benefit of and priority to U.S. Provisional Application Ser. No. 62/376,434, filed on Aug. 18, 2016 the entire contents of which are incorporated herein by reference.

BACKGROUND

Technical Field

The present disclosure relates to surgical forceps and, more particularly, to an endoscopic surgical forceps configured for treating and/or cutting tissue.

Background of Related Art

A surgical forceps is a pliers-like device which relies on mechanical action between its jaw members to grasp, clamp, and constrict tissue. Typically, at least one handle or lever is used to open and close the jaw members, and to provide compression force on tissue between the jaw members, to lock the jaw members in a closed position, and/or to apply energy to the jaw members to seal the tissue disposed therebetween.

Generally, such handles and levers used on surgical instruments are one of two types. One type is a simple pivoted handle that provides a near constant mechanical advantage throughout its stroke, and which is useful in many surgical situations. The second type of handle includes an additional link to provide a geometrically increasing mechanical advantage toward the end of its stroke to help provide the force necessary to compress tissue.

Both of these types of handles fix the mechanical advantage of the drive system such that the drive system cannot be optimized independently over the entire lever stroke. Often times, it may be desirable for a system to include fine dissection capability (a relatively large amount of handle travel for a relatively small amount of jaw member movement) when the jaw members are in an initial, or open position, and to include a high mechanical advantage while applying compression force to tissue disposed between the jaw members when the jaw members are in or near their approximated position (to help reduce surgeon fatigue, for instance). However, current handles are generally unable to achieve both of these desires in a single system.

SUMMARY

The present disclosure relates to a surgical instrument including a housing, an elongated shaft extending distally from the housing and defining a longitudinal axis, an end effector assembly, and a trigger assembly. The end effector assembly is disposed adjacent a distal end of the elongated shaft, and includes a first jaw member and a second jaw member. One or both of the jaw members is movable with respect to the other jaw member from a spaced-apart position to a position closer to the other jaw member for grasping tissue. The trigger assembly is disposed in mechanical cooperation with the housing and is configured to longitudinally translate a drive member. The trigger assembly includes a trigger, a gear assembly, a spool, a slider, and a flexible drive member. The trigger is disposed in mechanical cooperation with the gear assembly. The flexible drive member is configured to engage the gear assembly, the spool, and the slider. Movement of the trigger with respect to the housing results in movement of the flexible drive member with respect to the housing and longitudinal movement of the slider with respect to the housing.

In aspects of the present disclosure, the surgical instrument further includes a drive assembly disposed at least partially within the housing. The drive assembly includes a drive bar extending at least partially through the elongated shaft such that longitudinal translation of the drive bar causes the jaw members to move between the spaced-apart position and the closer position for grasping tissue.

In other aspects, the drive bar is rotatable about the longitudinal axis with respect to the housing. In yet other aspects, the drive bar is rotatable about the longitudinal axis with respect to the slider.

In still other aspects, the trigger assembly further includes a ring. The ring is rotationally supported by the slider. In aspects of the present disclosure, the ring is rotationally fixed with respect to the drive bar. In other aspects, the ring is longitudinally translatable with respect to the drive bar.

In yet other aspects, the drive member is longitudinally translatable with respect to the drive bar. In still other aspects, the drive bar is rotatable with respect to the drive member.

In aspects of the present disclosure, the gear assembly includes a first gear and a second gear. The first gear is configured to engage the trigger, and the second gear is configured to engage the spool.

The present disclosure also relates to a trigger assembly for use with a surgical instrument. The trigger assembly includes a trigger, a gear assembly disposed in mechanical cooperation with the trigger, a spool, a slider, and a flexible drive member. The flexible drive member is configured to engage the gear assembly, the spool, and the slider. Actuation of the trigger results in movement of the flexible drive member with respect to the spool and longitudinal movement of the slider with respect to the spool.

In aspects of the present disclosure, the trigger assembly includes a ring rotationally supported by the slider. In other aspects, the ring is longitudinally translatable with respect to the spool.

In still other aspects, the gear assembly includes a first gear and a second gear. The first gear is configured to engage the trigger, and the second gear is configured to engage the spool. In yet other aspects, the first gear and the second gear are rotationally fixed with respect to each other.

In aspects of the present disclosure, the flexible drive member is in contact with the spool and the slider.

In other aspects, the spool includes a spool gear having a plurality of teeth configured to engage a portion of the gear assembly.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
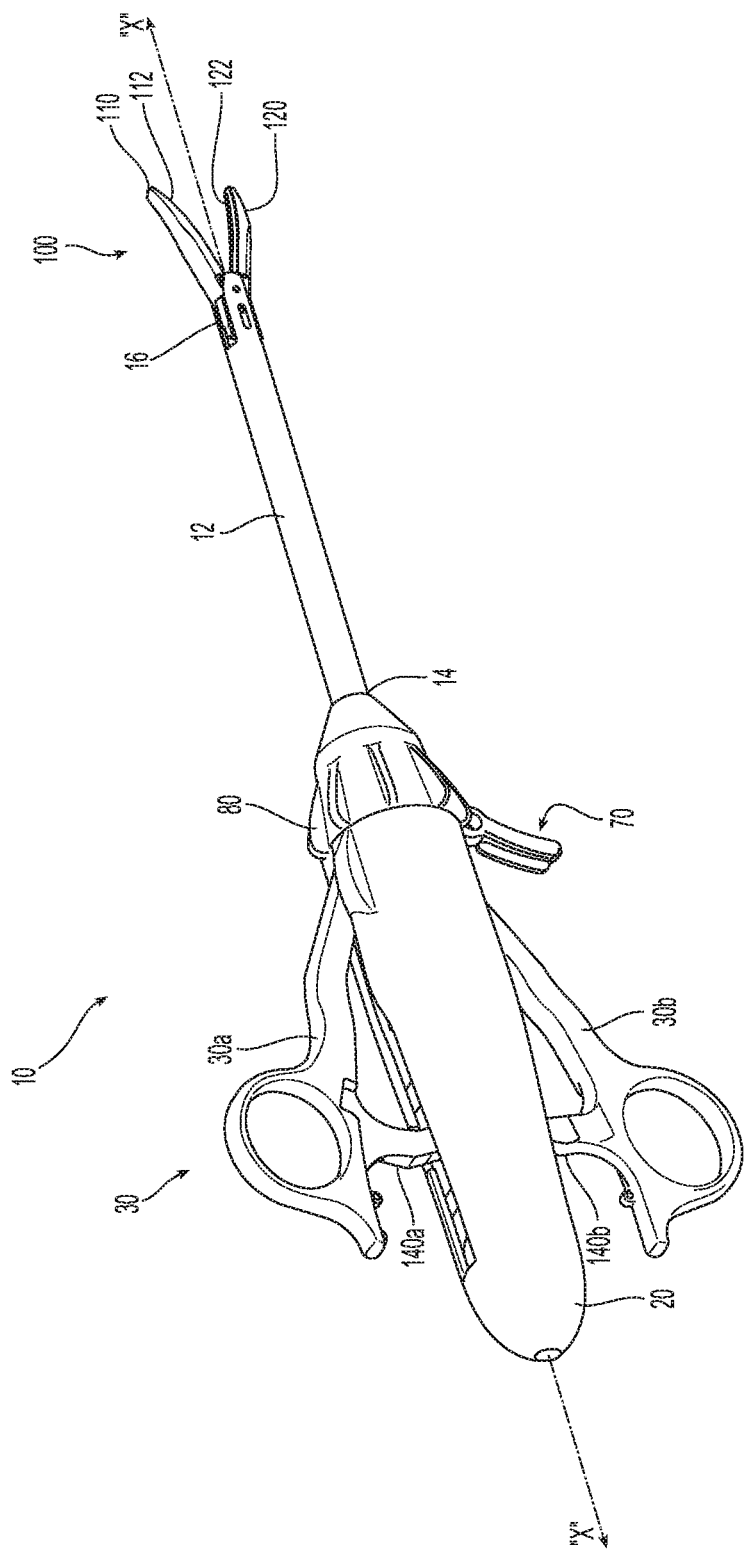
FIG. 1 is a perspective view of a surgical forceps provided in accordance with the present disclosure.

Embodiments of the presently disclosed surgical forceps are described in detail with reference to the drawings, in which like reference numerals designate identical or corresponding elements in each of the several views. As used herein the term "distal" refers to that portion of the surgical forceps that is farther from the user, while the term "proximal" refers to that portion of the surgical forceps that is closer to the user.

With initial reference to FIG. 1, an embodiment of a surgical forceps in accordance with the present disclosure is shown generally identified by reference character 10. Although surgical forceps 10 is shown configured for use in connection with endoscopic surgical procedures, the present disclosure is equally applicable for surgical instruments used in open surgical procedures and in connection with any suitable surgical instrument. For the purposes herein, forceps 10 is generally described.

Forceps 10 is adapted for use in various surgical procedures and generally includes a housing 20, a handle assembly 30, a trigger assembly 70, a rotating assembly 80, and an end effector assembly 100. Jaw members 110 and 120 of end effector assembly 100 mutually cooperate to grasp, treat, seal and/or cut tissue. Forceps 10 further includes a shaft 12 having a distal end 16 that mechanically engages end effector assembly 100, and a proximal end 14 that mechanically engages housing 20. Forceps 10 may be configured to connect to a source of energy, e.g., a generator (not shown), forceps 10 may be configured as a battery powered instrument, or forceps 10 may be manually powered (e.g., when providing electrosurgical energy is not desired).

Figure 2:
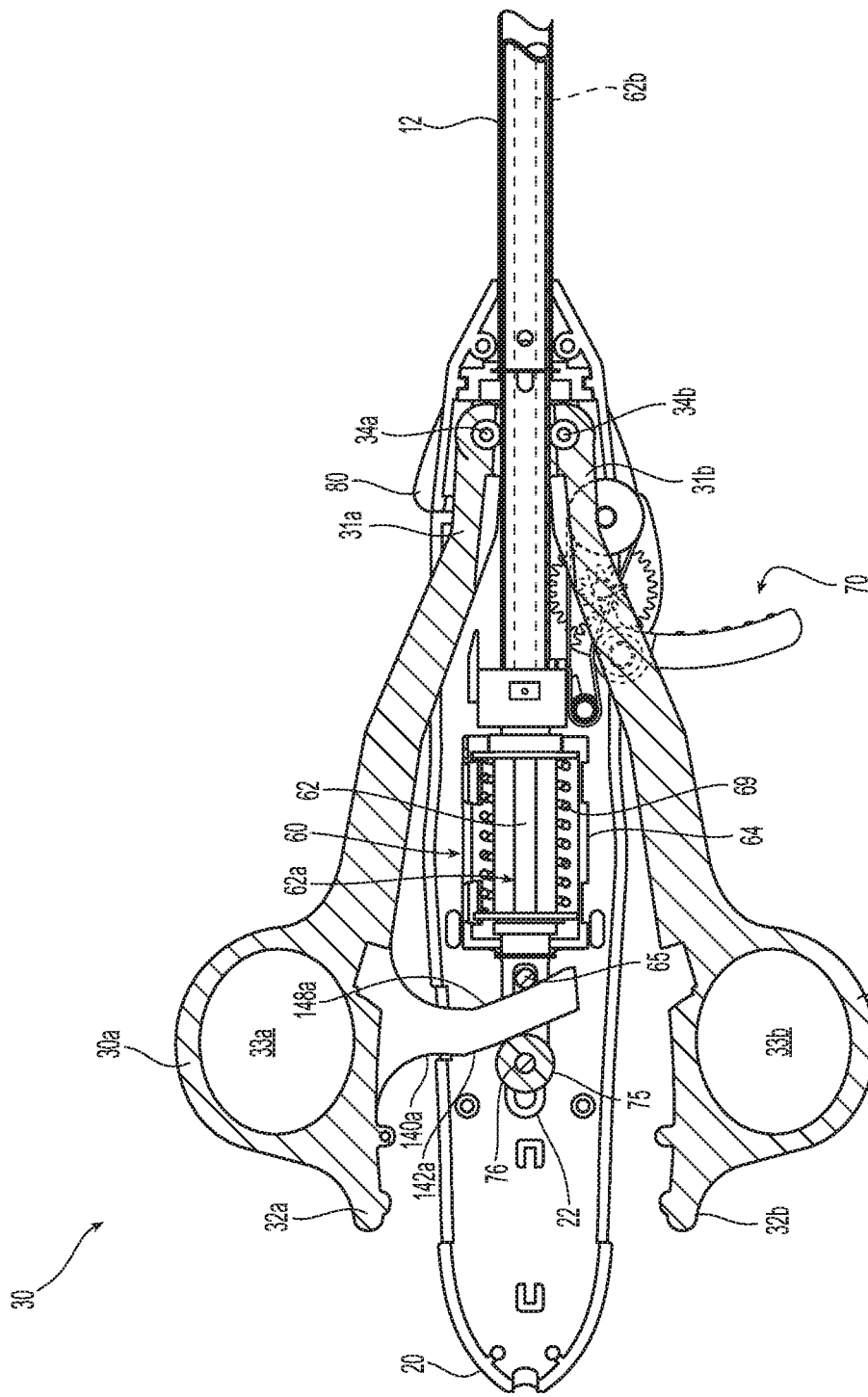
FIG. 2 is a sectional view of a handle assembly of the surgical forceps of FIG. 1 where a first cam of a first handle is shown, and where a second cam of a second handle is omitted.
Figure 3:
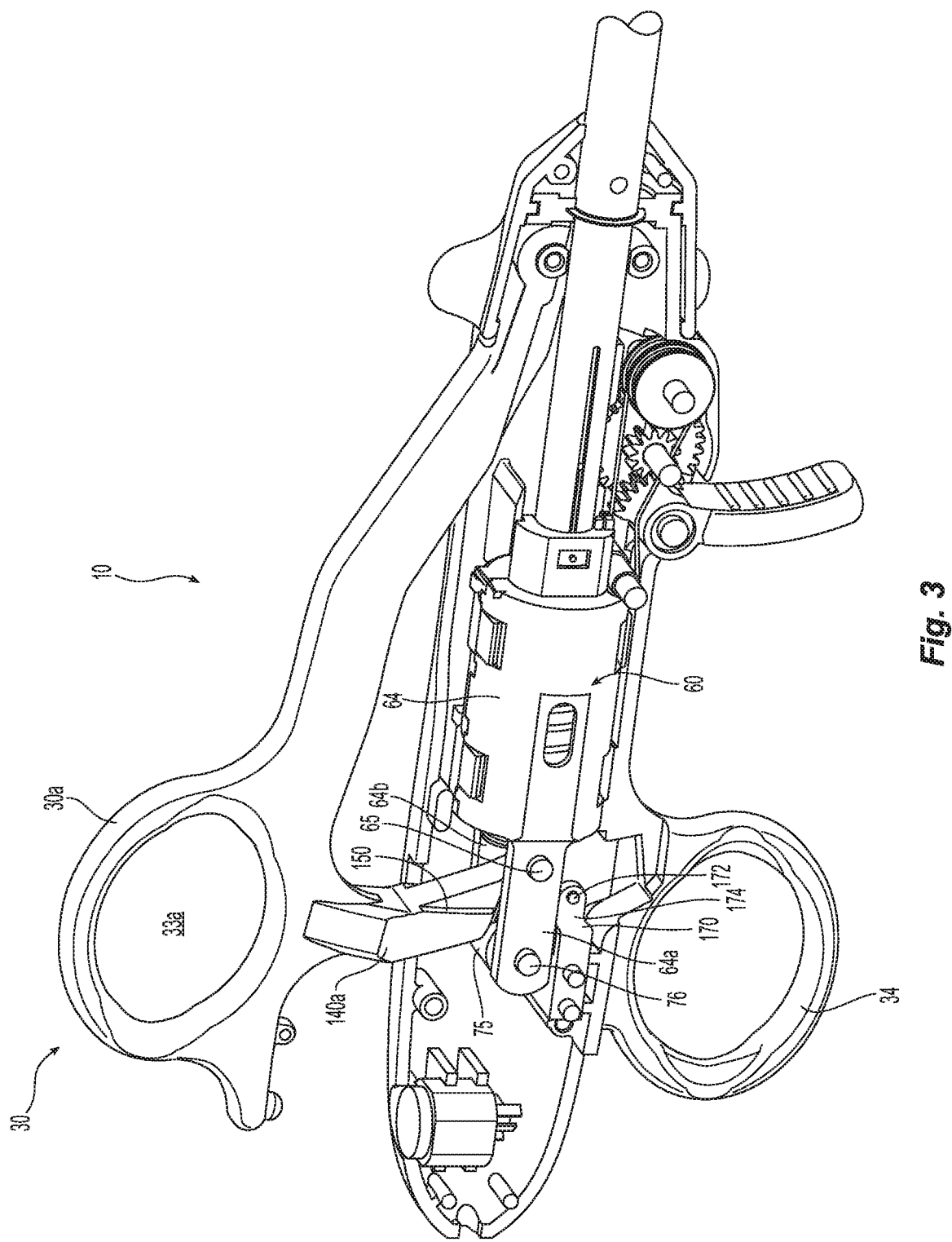
FIGS. 3-6 are perspective views of internal components of the handle assembly of FIGS. 1 and 2.

As shown in FIGS. 1 and 2, for example, handle assembly 30 includes a first movable handle 30a and a second movable 30b disposed on opposite sides of housing 20. Handles 30a and 30b are movable relative to one another to actuate end effector assembly 100, as will be described in greater detail below. Further, while two movable handles 30a and 30b are shown and described herein, the present disclosure also includes handle assembly 30 including a single movable handle, as shown in FIGS. 3-16, for example. Here, in addition to the single movable handle, a finger loop 34 is included on the opposite side of housing 20 as the single movable handle. Additionally, handle 30b may include the same, mirror-image, or corresponding features as handle 30a.

Rotating assembly 80 is mechanically coupled to housing 20 and is rotatable in either direction, to rotate shaft 12 and, thus, end effector assembly 100 about a longitudinal axis "X" defined by shaft 12. Such a configuration allows end effector assembly 100 to be rotated in either direction with respect to housing 20.

Handle(s) 30a and/or 30b of handle assembly 30 ultimately connect to a drive assembly 60 disposed within housing 20 and that extends through shaft 12 which, together, cooperate to impart movement of jaw members 110 and 120 from an open position wherein jaw members 110 and 120 are disposed in spaced relation relative to one another, to a closed or approximated position wherein jaw members 110 and 120 cooperate to grasp tissue therebetween.

Handles 30a and 30b of handle assembly 30 each include a finger loop or an aperture 33a and 33b, respectively, defined therein which enables a user to grasp and move handles 30a and 30b relative to one another and relative to housing 20 between a spaced-apart position and an approximated position. In the embodiment where handle assembly 30 includes two handles 30a and 30b, each handle 30a and 30b is pivotably coupled to housing 20 at its respective distal end 31a, 31b via pivot pins 34a, 34b, respectively, and extends proximally to proximal ends 32a, 32b, respectively, thereof. As mentioned above, handles 30a, 30b are coupled to drive assembly 60 such that pivoting of handles 30a, 30b about pivot pins 34a, 34b, respectively, and relative to one another effects pivoting of jaw members 110, 120 between the open and closed positions, as discussed in further detail below. In the embodiment where handle assembly 30 includes a single movable handle 30a and a finger loop 34, handle 30a is pivotably coupled to housing at its distal end 31a via pivot pin 34b. Here, movement of handle 30a with respect to housing 20 effects pivoting of jaw members 110, 120 between the open and closed positions.

With particular reference to FIG. 2, drive assembly 60 includes a drive bar 62 defining a proximal end 62a disposed within housing 20 and a distal end 62b that extends through shaft 12, ultimately coupling to jaw members 110, 120. A mandrel 64 disposed within housing 20 is engaged with the proximal end 62a of drive bar 62. Mandrel 64 is slidably engaged with at least one track 22 (see FIG. 2) defined within housing 20 to guide longitudinal translation of mandrel 64 and, thus, drive bar 62, relative to housing 20. Other suitable guide/alignment mechanisms are also contemplated. A spring 69 is positioned within mandrel 64 and is configured to prevent over compression of tissue when jaw members 110, 120 are in the closed or approximated position.

A follower 75 is rotatably supported by an axle 76, which extends through a bore of follower 75. Axle 76 is supported (e.g., rotatably supported) by proximal extensions 64a, 64b of mandrel 64. A cam follower (e.g., a pin within a sleeve) 65 is also supported (e.g., rotatably supported) by proximal extensions 64a, 64b of mandrel 64.

While the following description discusses the use of two handles 30a, 30b, the use of a single handle 30a may also be utilized without departing from the scope of the present disclosure. In order to move jaw members 110, 120 from the open position to the closed position, handles 30a and/or 30b are squeezed, e.g., pivoted about pivot pins 34a, 34b, inwardly towards one another and housing 20. As handle(s) 30a, 30b are pivoted in this manner, proximal ends 32a, 32b of handles 30a, 30b are approximated relative to housing 20 and one another. The approximation of proximal ends 32a, 32b of handles 30a, 30b towards one another causes extensions 140*a*, 140*b* of respective handles 30*a*, 30*b* to urge follower 75, mandrel 64 and drive bar 62 proximally, thus approximating jaw members 110, 120. Movement of handles 30*a*, 30*b* toward their open position causes extensions 140*a*, 140*b* to urge cam follower 65, mandrel 64 and drive bar 62 distally, thus causing jaw members 110, 120 to move toward their open position, as further described below. The spring force of spring 69 may be configured such that jaw members 110, 120 impart a closure force between jaws within a range of about 3 kg/cm$^2$ to about 16 kg/cm$^2$, although other closure forces are also contemplated.

Additionally, with reference to FIGS. 3-6, extension 140*a* includes a rib 150 thereon. The shape of rib 150 is arcuate when used with a pivoting handle 30*a*; rib 150 may be linear when used with a non-pivoting handle (not shown). Rib 150 is configured to be contacted by a roller 160.

Figure 4:
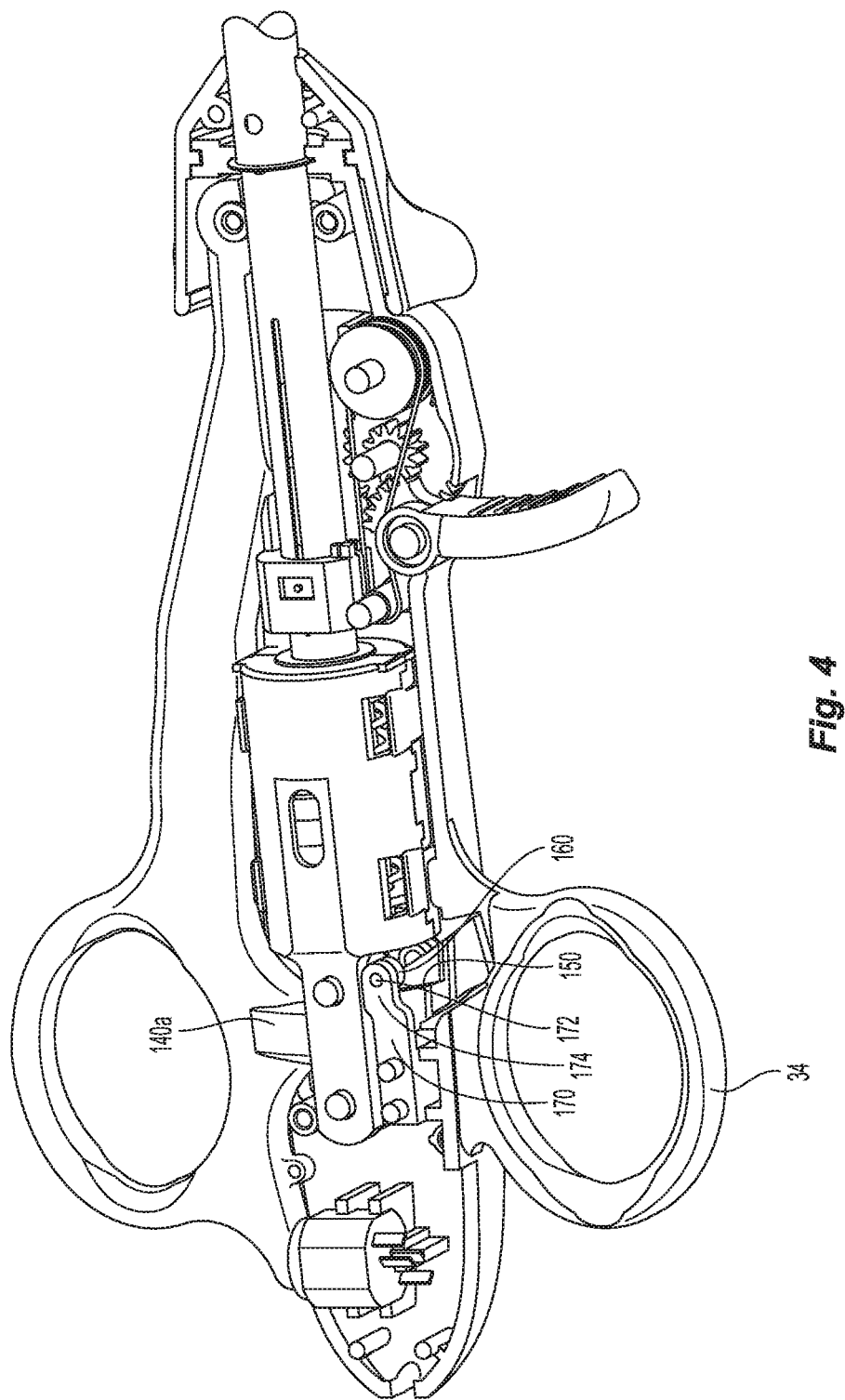
Figure 5:
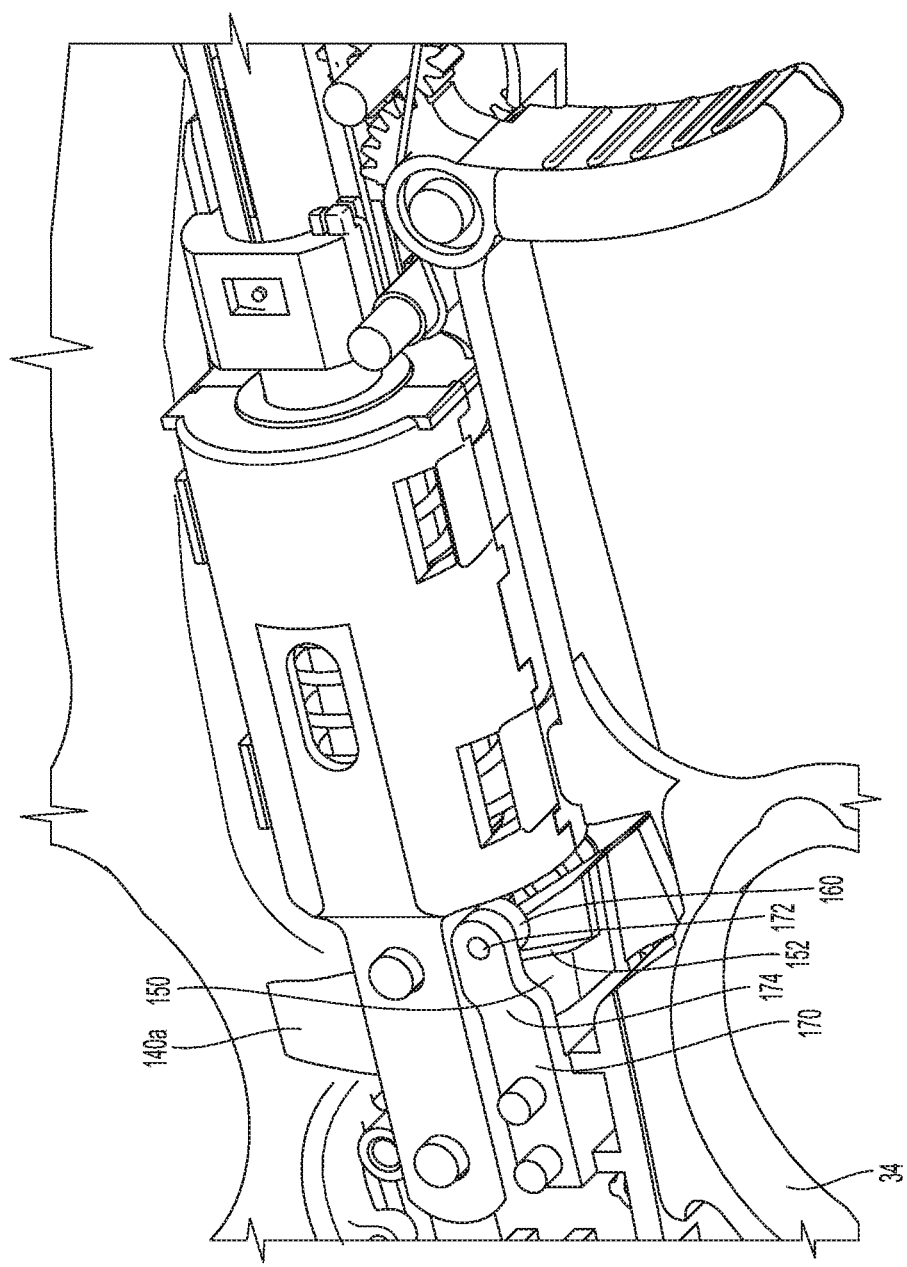
Figure 6:
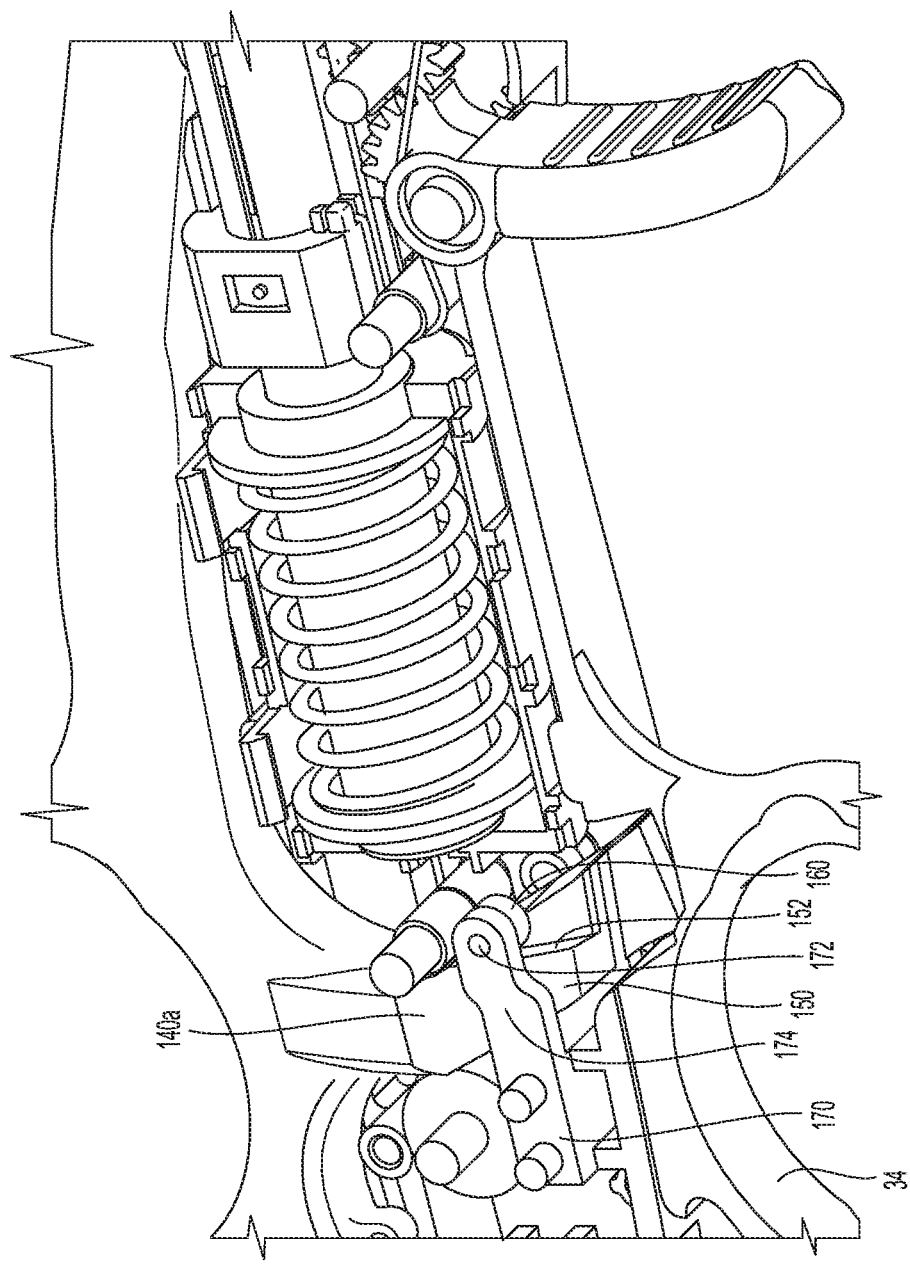

As shown in FIGS. 4-6, roller 160 is supported by a support 170. Support 170 is fixed to housing 20 of surgical forceps 10 and includes a pin 172 extending through a leg 174 of support 170. Pin 172 rotationally supports roller 160. Roller 160 is longitudinally fixed with respect to housing 20 and is configured to engage rib 150 of extension 140*a*.

As handle 30*a*, and thus extension 140*a*, is moved, roller 160 moves along rib 150. More particularly, as handle 30*a* is moved, roller 160 contacts and thus supports a distal wall 152 of rib 150. For example, when handle 30*a* is moved generally downward (as viewed in FIG. 3) to approximate the jaw members, for instance, roller 160 contacts distal wall 152 of rib 150. Thus, roller 160 provides support to rib 150, and thus handle 30*a*, during approximation of jaw members, e.g., to restrict or minimize unintended bending or flexing motion in extension 140*a*, handle 30*a*, and other features within housing 20.

Figure 6A:
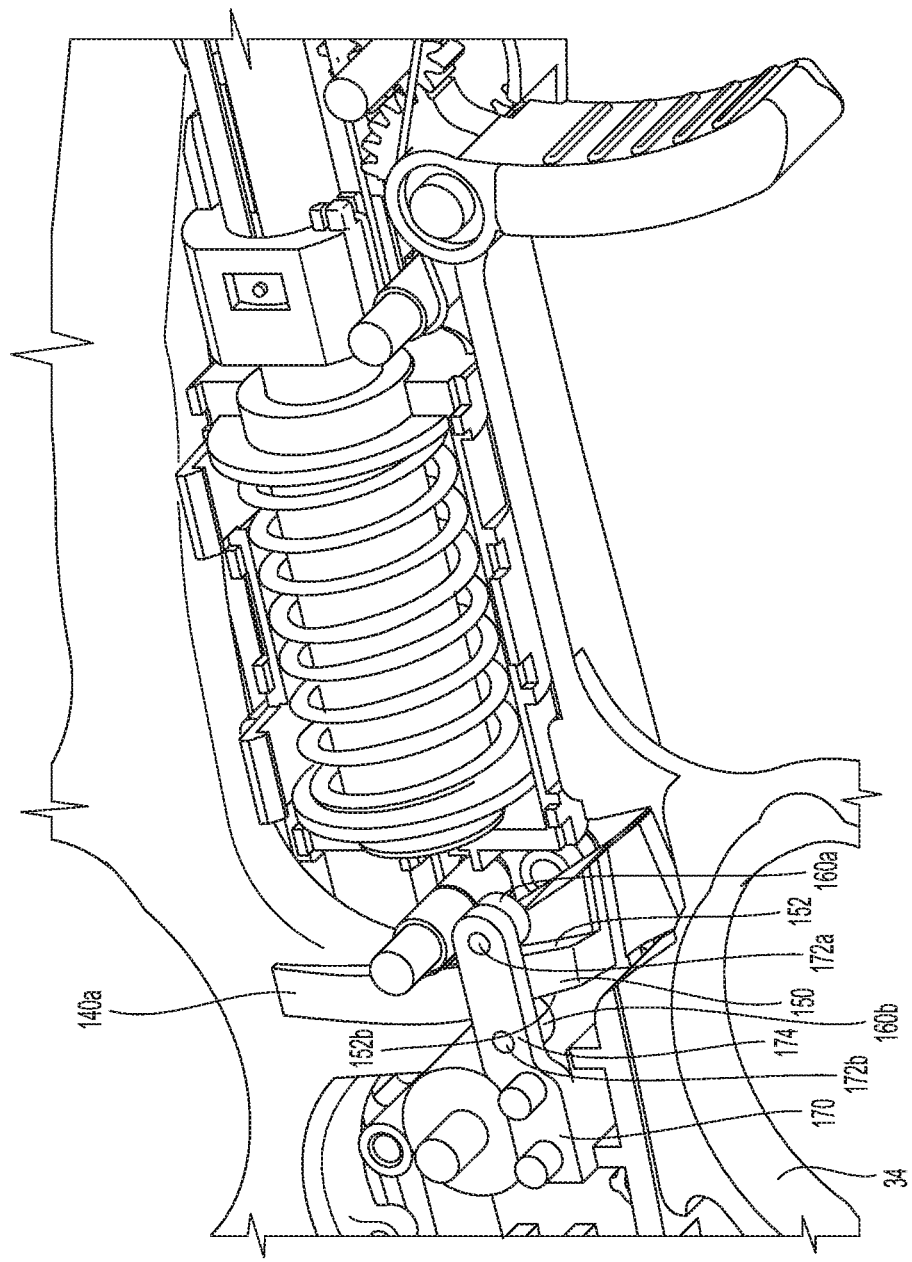
FIG. 6A is a perspective view of internal components of a handle assembly according to an embodiment of the present disclosure.

An alternate embodiment is shown in FIG. 6A, which includes a first roller 160*a* and a second roller 160*b*. Each of first roller 160*a* and second roller 160*b* is supported by support 170. Support 170 is fixed to housing 20 of surgical forceps 10 and includes a first pin 172*a* and a second pin 172*b* extending through leg 174 of support 170. First pin 172*a* rotationally supports first roller 160*a*, and second pin 172*b* rotationally supports second roller 160*b*. First and second rollers 160*a*, 160*b* are longitudinally fixed with respect to housing 20 and are configured to engage rib 150 of extension 140*a*.

As handle 30*a*, and thus extension 140*a*, is moved, first and second rollers 160*a*, 160*b* move along rib 150. More particularly, as handle 30*a* is moved, first roller 160*a* contacts and thus supports distal wall 152 of rib 150. For example, when handle 30*a* is moved generally downward (as viewed in FIG. 3) to approximate the jaw members, for instance, first roller 160*a* contacts distal wall 152 of rib 150. Thus, first roller 160*a* provides support to rib 150, and thus handle 30*a*, during approximation of jaw members, e.g., to restrict or minimize unintended bending or flexing motion in extension 140*a*, handle 30*a*, and other features within housing 20. Additionally, when handle 30*a* is moved generally upward (as viewed in FIG. 3) to open the jaw members, for instance, second roller 160*b* contacts a proximal wall 152*b* of rib 150. Thus, second roller 160*b* provides support to rib 150, and thus handle 30*a*, during opening of jaw members, e.g., to restrict or minimize unintended bending or flexing motion in extension 140*a*, handle 30*a*, and other features within housing 20.

During use, a surgeon may desire fine (vs. gross) control of jaw members 110, 120 during some stages of use. For example, the surgeon may wish to have greater control of the movement of the jaw members 110, 120 during dissection of tissue, manipulation of tissue, and precise placement of jaw members 110, 120 about target tissue. For such fine control of jaw members 110, 120, a relative large amount of travel of handles 30*a*, 30*b* (or a single handle) would correspond to a relative small amount of travel of jaw members 110, 120. Some surgeons may also desire to have a high mechanical advantage during other stages of use. For example, a surgeon may wish to utilize a high mechanical advantage while applying compression force to tissue. To achieve such a high mechanical advantage, a relative small amount of travel of handles 30*a*, 30*b* would correspond to a relative large amount of travel of jaw members 110, 120. Typically, surgical instruments only allow for either fine control of jaw members 110, 120 or a high mechanical advantage. Examples of one surgical forceps configured to allow both fine control of jaw members and a high mechanical advantage at different stages of the actuation stroke of handles is described in U.S. Provisional Patent Application Ser. No. 62/247,279, filed on Oct. 28, 2015, the entire contents of which is incorporated by reference herein.

Figure 7:
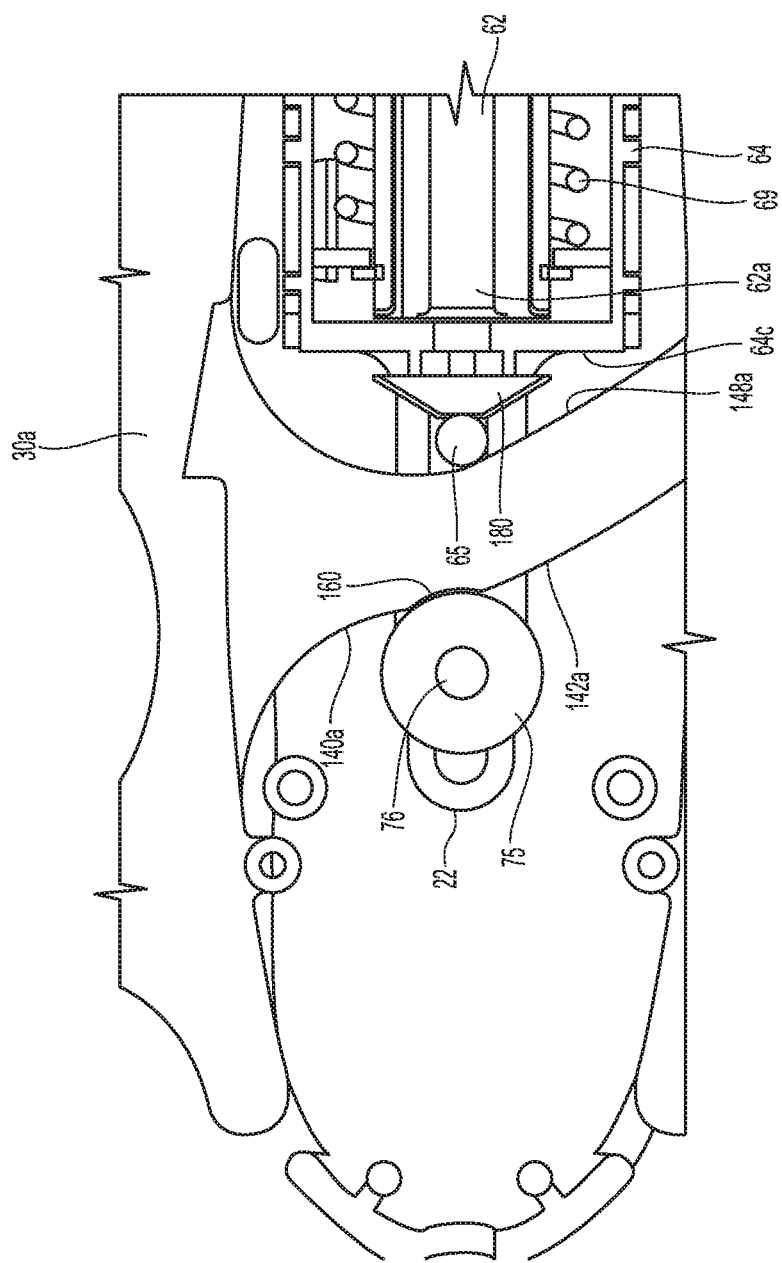
FIG. 7 is a sectional view of internal components of the handle assembly of FIGS. 1-6.
Figure 8:
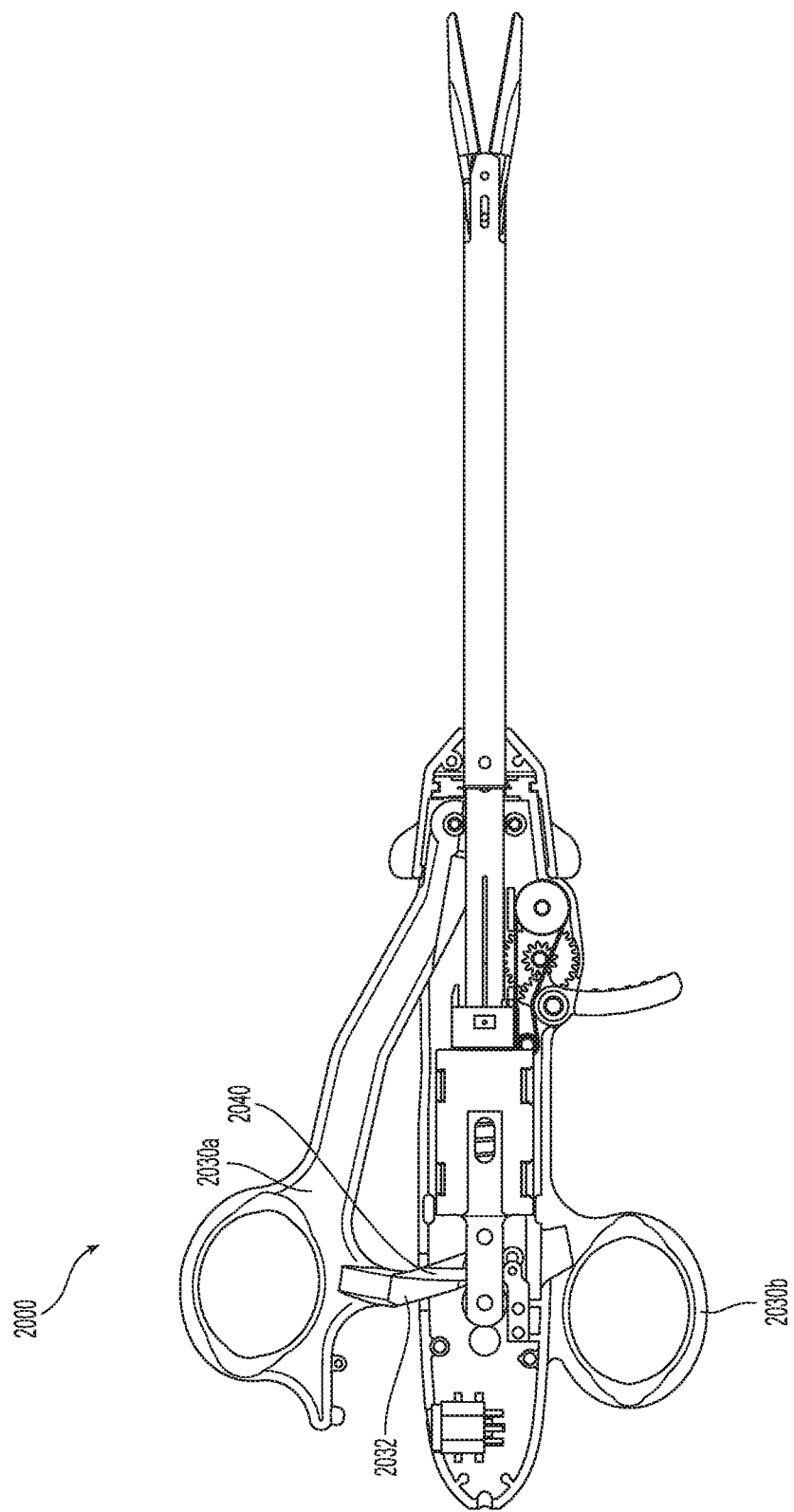
FIG. 8 is a sectional view of another embodiment of a surgical forceps provided in accordance with the present disclosure.
Figure 9:
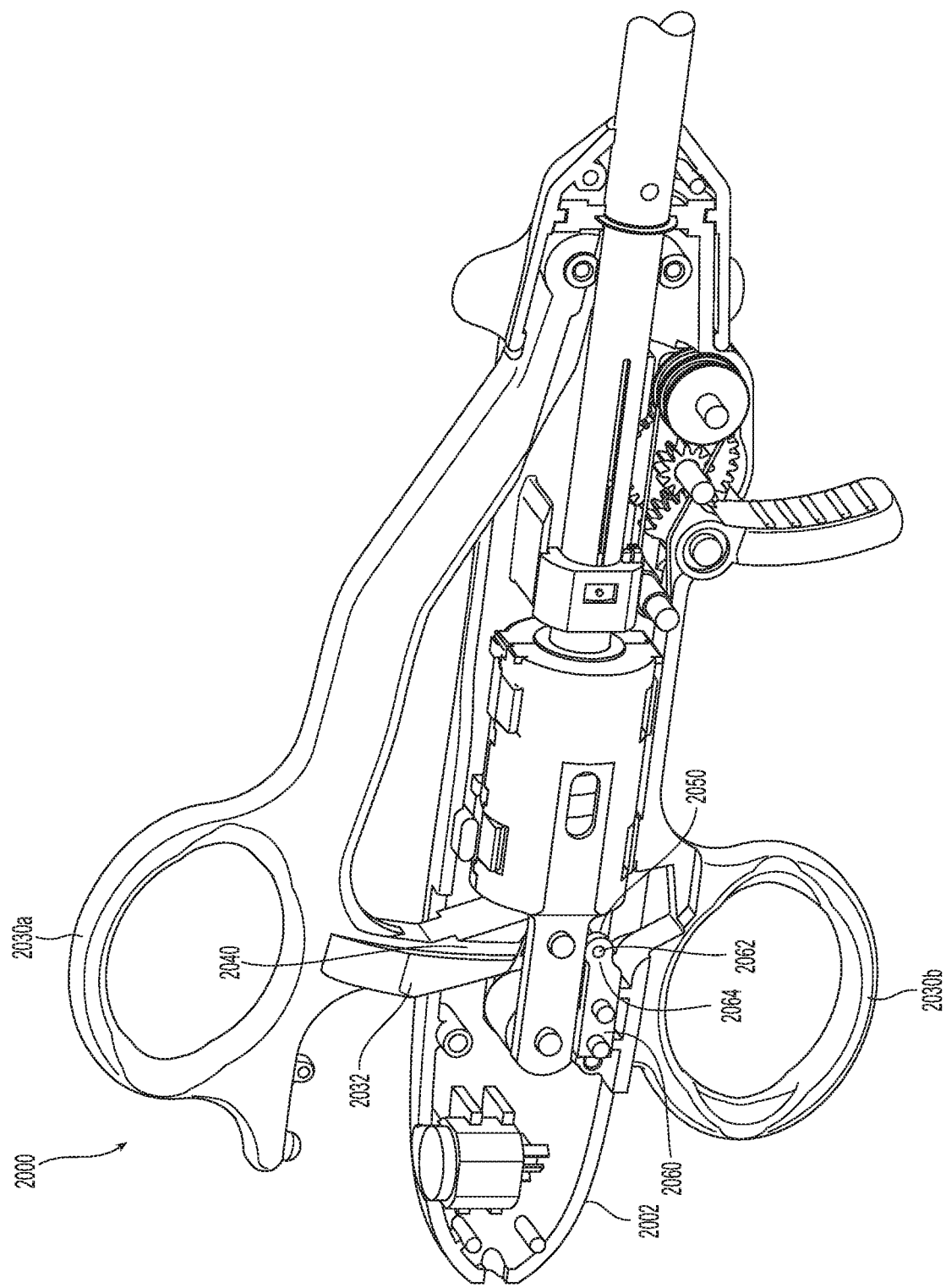
FIGS. 9-12 are perspective views of internal components of a handle assembly of the surgical forceps of FIG. 8.
Figure 10:
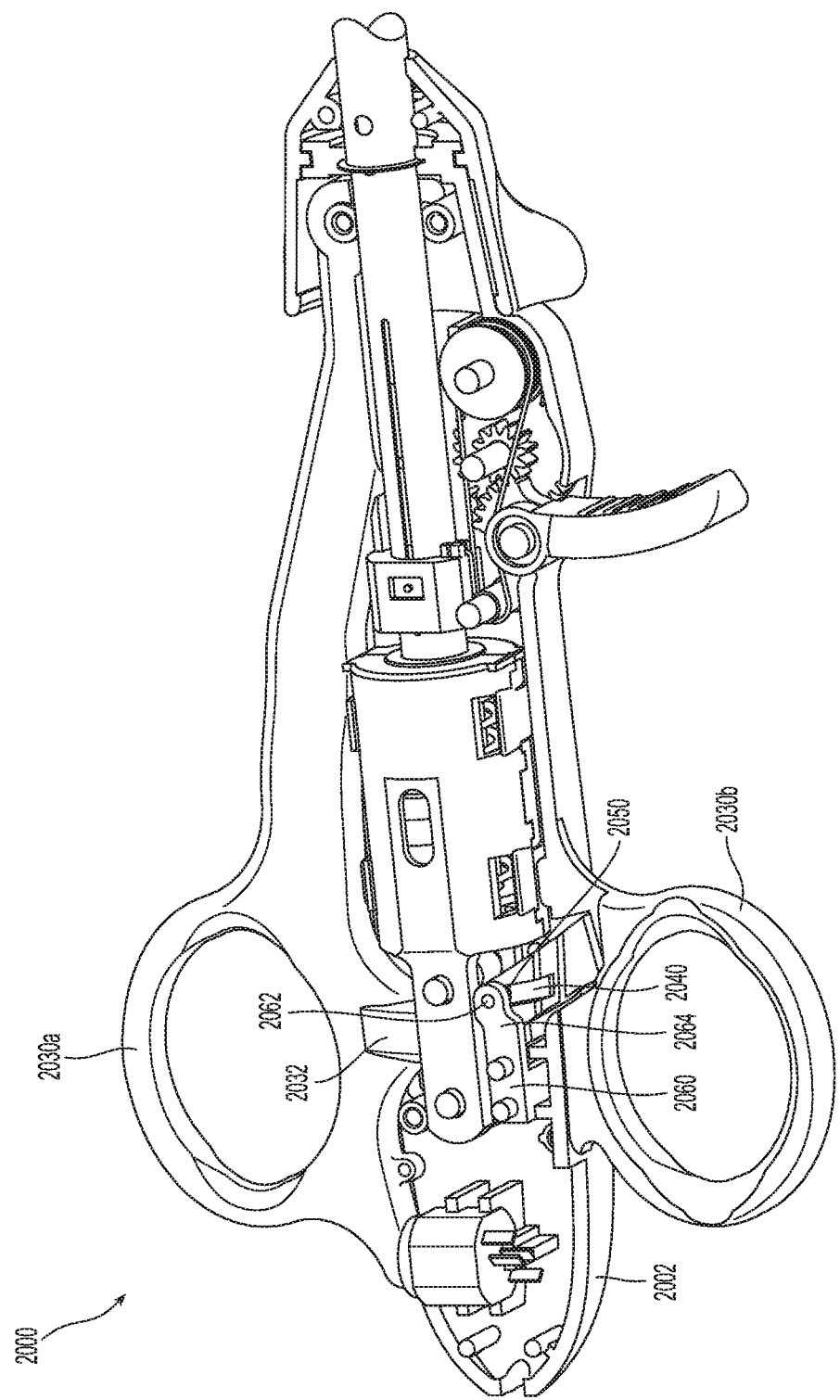

With particular reference to FIG. 7, to help ensure that contact is maintained between follower 75 and a proximal cam surface 142*a*, and between cam follower 65 and a distal cam surface 148*a* (e.g., to account for manufacturing tolerances, and/or to allow greater manufacturing tolerances, thus reducing costs), surgical forceps 10 may include an engagement spring 180 disposed between a proximal wall 64*c* of mandrel 64 and cam follower 65. Engagement spring 180 is configured to urge cam follower 65 proximally toward and into contact with distal cam surface 148*a*. Engagement spring 180 may be cone-like (e.g., frusto-conical) in shape, or a so-called Belleville washer.

With particular reference to FIGS. 8-12, an additional embodiment of surgical forceps is shown and is indicated by reference character 2000. Surgical forceps 2000 is similar to surgical forceps 10 discussed above and only the differences are discussed in detail herein.

Surgical forceps 2000 includes a movable handle 2030*a* and a finger loop 2030*b*. In lieu of finger loop 2030*b*, surgical forceps 2000 may include a second movable handle. Handle 2030*a* includes an extension 2032 having a groove or channel 2040 defined therein. A roller 2050 is movably positioned within channel 2040.

Figure 11:
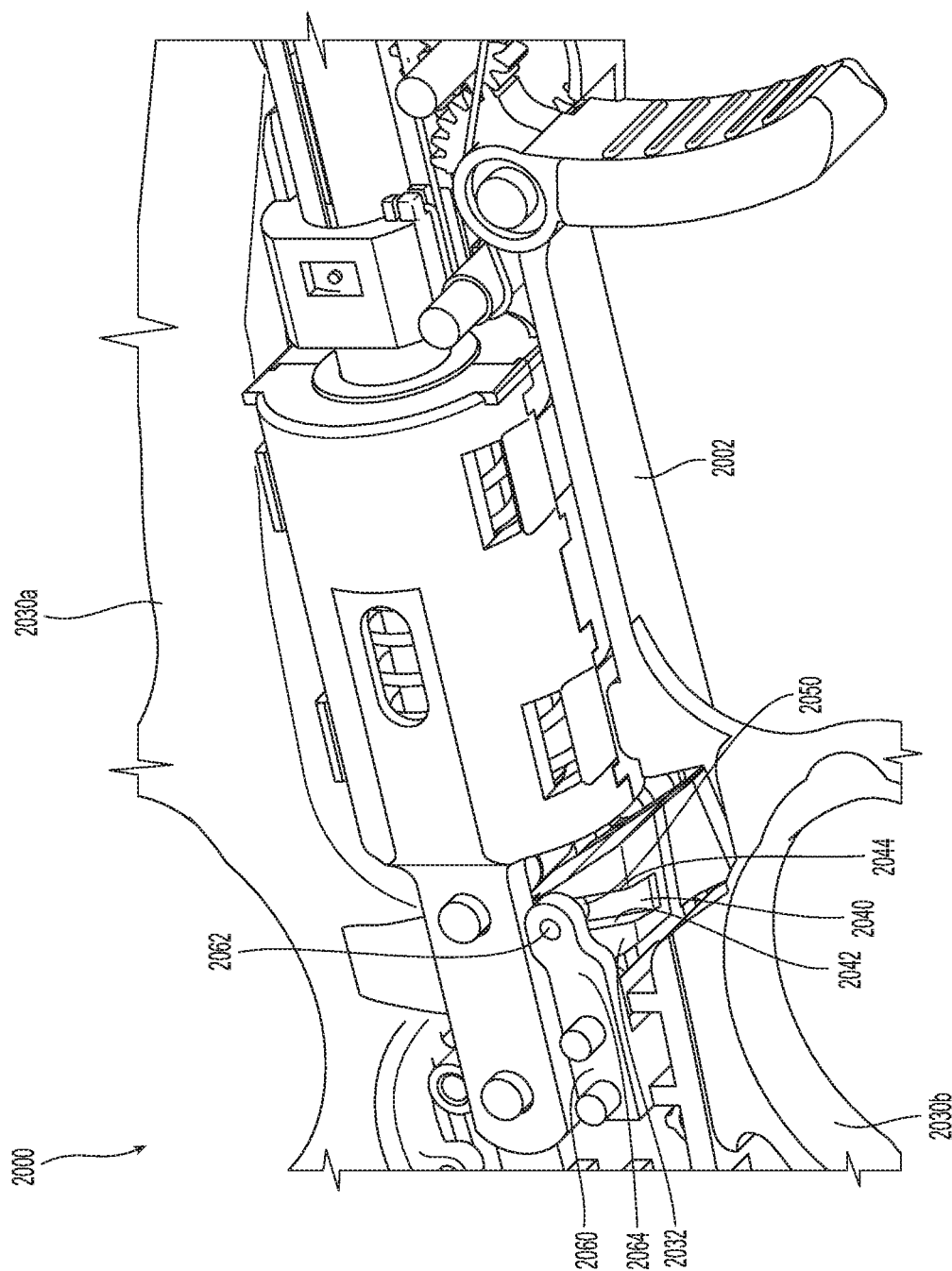
Figure 12:
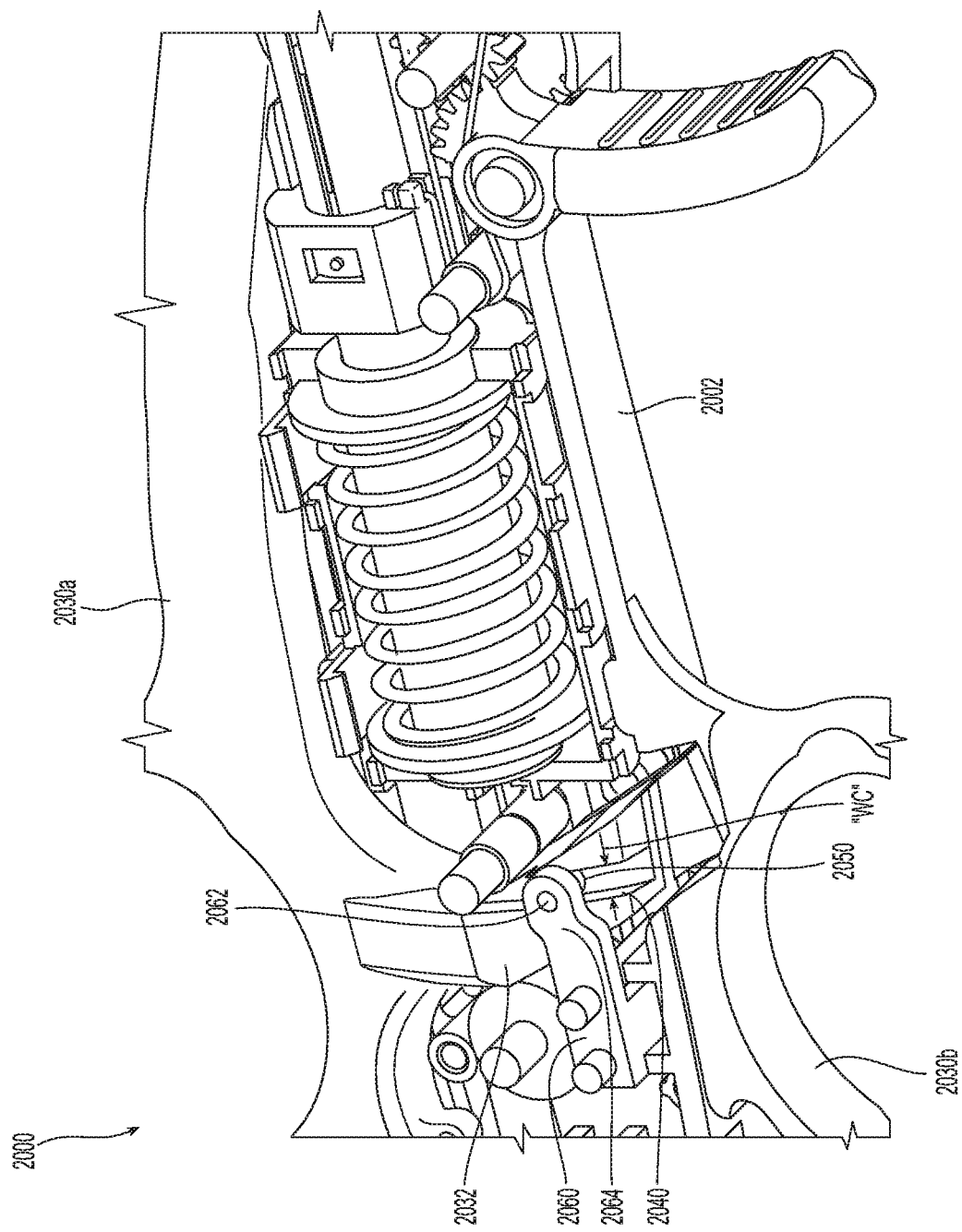
Figure 13:
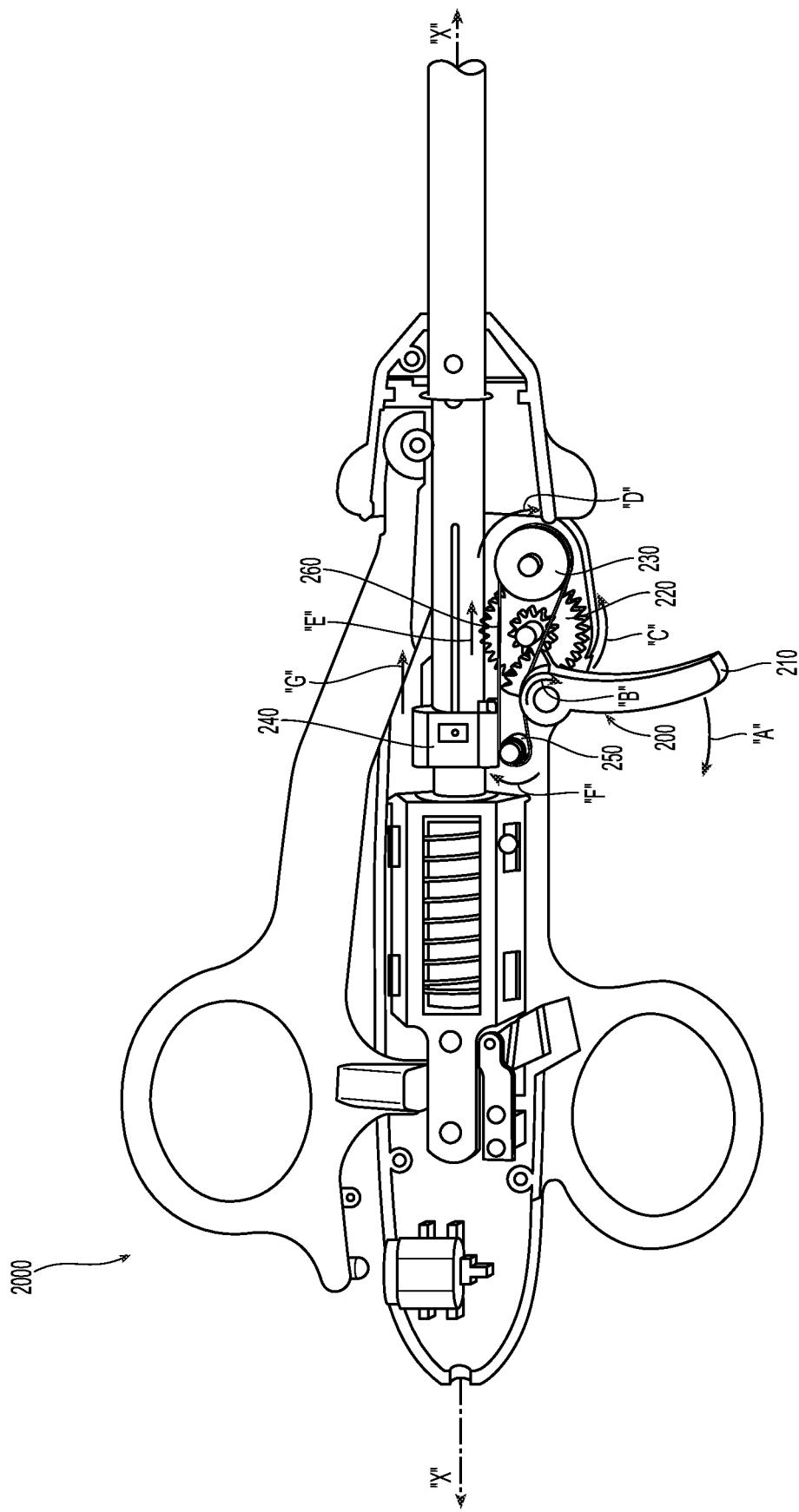
FIG. 13 is a sectional view of a handle assembly of another embodiment of a surgical forceps provided in accordance with the present disclosure.

More particularly, channel 2040 extends within extension 2032 of handle 2030*a* and is defined by a proximal wall 2042 and a distal wall 2044 (FIG. 11). The shape of channel 2040 is arcuate when used with a pivoting handle 2030*a*; channel 2040 may be linear when used with a non-pivoting handle (not shown). Channel 2040 includes a width "wc" (FIG. 12) which may be uniform along its entire length or which may vary along at least a portion of its length.

Roller 2050 is supported by a support 2060. Support 2060 is fixed to housing 2002 of surgical forceps 2000 and includes a pin 2062 extending through a leg 2064 of support 2060. Pin 2062 rotationally supports roller 2050. Roller 2050 is longitudinally fixed with respect to housing 2002 and is configured to engage channel 2040 of extension 2032. Roller 2050 includes a width in the longitudinal direction. The width of roller 2050 is smaller than width "wc" of channel 2040, thus enabling roller 2050 to move within channel 2040.

As handle 2030*a*, and thus extension 2032, is moved, roller 2050 moves within channel 2040. More particularly, as handle 2030*a* is moved, roller 2050 contacts proximal wall 2042 and distal wall 2044 of channel 2040. For example, when handle 2030*a* is moved generally downward (as viewed in FIG. 8) to approximate the jaw members, for instance, roller 2050 may contact distal wall 2044 of channel 2040; when handle 2030a is moved generally upward (as viewed in FIG. 8) to move the jaw members to the open position, roller 2050 may contact proximal wall 2042 of channel 2040. Thus, channel 2040 provides support to roller 2050 at all times during manipulation of the jaw members, e.g., to restrict or minimize unintended bending motion.

The difference between the width of roller 2050 and the width "wc" of channel 2040 determines the amount of travel or "play" that handle 2030a can undergo while being actuated; a small difference between these distances results in a lower amount of "play."

Surgical forceps 10, 2000 may also include features to help maintain the handle(s) in the closed position, and may include features for providing feedback to the user at certain stages of approximating or opening the jaw members. Such features are described in U.S. Provisional Patent Application Ser. No. 62/247,279, filed on Oct. 28, 2015, the entire contents of which have been incorporated by reference hereinabove.

The present disclosure also includes methods of manipulating jaw members 110, 120 using fine and gross controls, as described above. For example, disclosed methods include moving handle 30a, 30b of surgical instrument 10 from a non-actuated position a first distance to an intermediate position to cause first jaw member 110 to move a first amount, and moving handle 30a, 30b from the intermediate position a second distance to a fully actuated position to cause first jaw member 110 to move a second amount. Here, the first distance is the same as the second distance, and the first amount is less than the second amount, thus resulting in an initial fine movement of jaw member 110, and a subsequent gross movement of jaw member 110.

With particular reference to FIGS. 13-16, details of a second type of trigger assembly 200 are shown. Trigger assembly 200 of this embodiment includes a trigger 210, a gear assembly 220, a drive spool 230, a knife slider 240, a roller 250, and a flexible drive member 260. As discussed below, actuation of trigger assembly 200 is configured to longitudinally translate a drive member (e.g., a knife drive shaft 244). Additionally, while trigger assembly 200 is shown used in connection with a particular surgical forceps 2000, trigger assembly 200 may also be used in connection with surgical forceps 10, or an additional type of surgical device.

Figure 14:
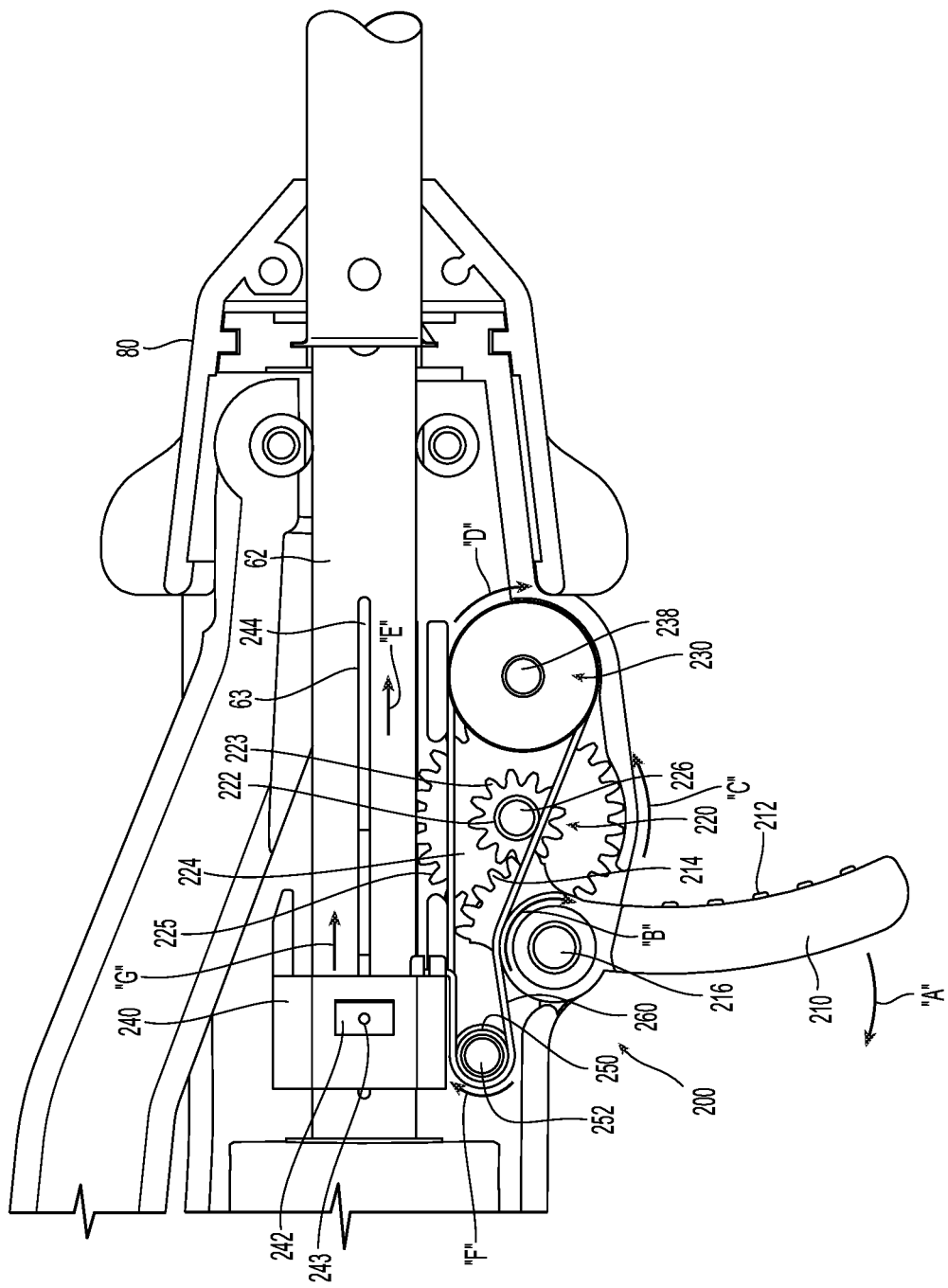
FIG. 14 is a sectional view of a trigger assembly of the surgical forceps of FIG. 13.
Figure 15:
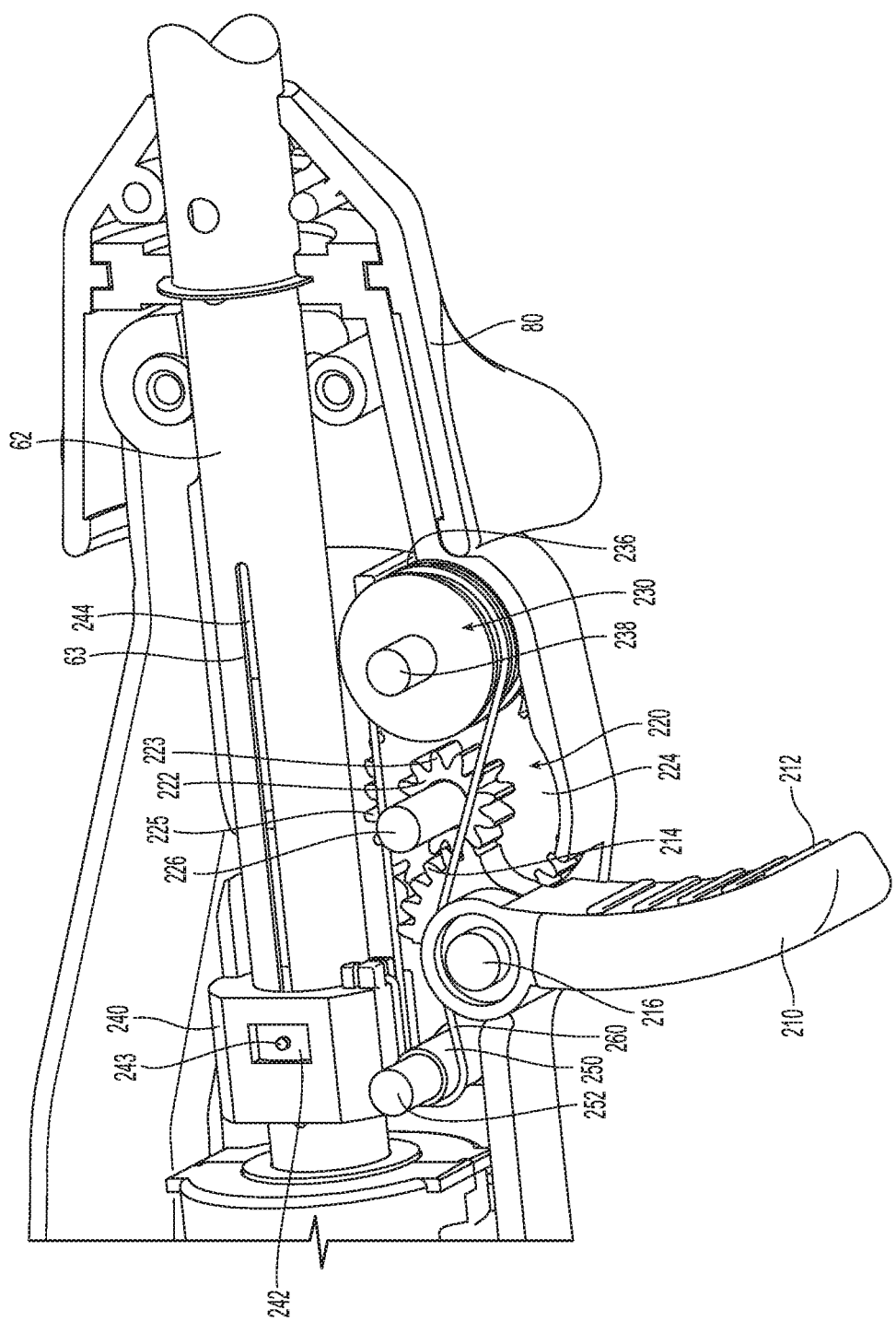
FIGS. 15 and 16 are perspective views of the trigger assembly of the surgical forceps of FIGS. 13-14.

With particular reference to FIGS. 14 and 15, trigger 210 includes an actuation portion 212 configured for direct engagement by the user (e.g., physician), a plurality of trigger teeth 214, and is rotatable about a trigger pin 216. Gear assembly 220 (e.g., a cluster gear) includes a first gear 222 having a plurality of teeth 223, and a second gear 224 having a plurality of teeth 225. First gear 222 and second gear 224 are rotationally fixed with respect to each other, and are rotatable about a gear pin 226.

Drive spool 230 includes a spool gear 232 having a plurality of teeth 234 (see FIG. 16), and spool portion 236. Drive spool 230 is rotatable about a spool pin 238. A knife ring 242 is rotationally disposed within a portion of knife slider 240. Knife ring 242 is rotatable about the longitudinal axis "X" with respect to knife slider 240. Roller 250 is rotatable about a roller pin 252. Flexible drive member 260 is in contact with spool portion 236 of drive spool 230, knife slider 240, and roller 250. Flexible drive member 260 can be made from any suitable material such as nylon, a para-aramid synthetic fiber (e.g., Kevlar®), high-modulus polyethylene (HMPE), etc. for example. Flexible drive member 260 can also be made from plastic, e.g., having a rectangular cross-section (such as a zip-tie). In such embodiments, the pushing of various elements may be facilitated due to the strength of plastic. Additionally, assembly of surgical forceps 2000 may be facilitated using a plastic flexible drive member 260, for example, as fewer loops may be necessary to accomplish each desired action (e.g., proximal and distal translation of knife slider 240.

Details regarding the various interactions between the components of trigger assembly 200 are discussed herein with continued reference to FIGS. 13-16. Trigger teeth 214 of trigger 210 engage or mesh with teeth 223 of first gear 222 of gear assembly 220. Accordingly, movement of actuation portion 212 in the general direction of arrow "A" in FIGS. 13 and 14 causes rotation of trigger teeth 214 about trigger pin 216 in the general direction of arrow "B" in FIGS. 13 and 14, which causes rotation of first gear 222 about gear pin 226 in the general direction of arrow "C" in FIGS. 13 and 14.

First gear 222 of gear assembly 220 is rotationally fixed with respect to second gear 224 of gear assembly 220. Teeth 225 of second gear 224 of gear assembly 220 engage or mesh with teeth 234 of spool gear 232 of drive spool 230. Accordingly, rotation of first gear 222 about gear pin 226 in the general direction of arrow "C" causes rotation of second gear 224 about gear pin 226 in the general direction of arrow "C," which causes rotation of spool gear 232 and drive spool 230 about spool pin 238 in the general direction of arrow "D" in FIGS. 13 and 14. Spool portion 236 of drive spool 230 is rotationally fixed with respect to spool gear 232, such that rotation of spool gear 232 causes a corresponding rotation of drive spool 230.

Flexible drive member 260 extends at least partially around spool portion 236 of drive spool 230, extends at least partially around roller 250, and is engaged with (e.g., wrapped around) a portion of knife slider 240. Flexible drive member 260 is longitudinally fixed with respect to knife slider 240. Accordingly, rotation of spool portion 236 of drive spool 230 in the general direction of arrow "D" causes translation of flexible drive member 260 in the general direction of arrow "E" in FIGS. 13 and 14, which causes roller 250 to rotate about roller pin 252 in the general direction of arrow "F" in FIGS. 13 and 14. Additionally, based on the way flexible drive member 260 engages a portion of knife slider 240 (as shown in FIG. 15), translation of flexible drive member 260 in the general direction of arrow "E" causes knife slider 240 to move in the general direction of arrow "G" (or distally) in FIGS. 13 and 14.

Figure 16:
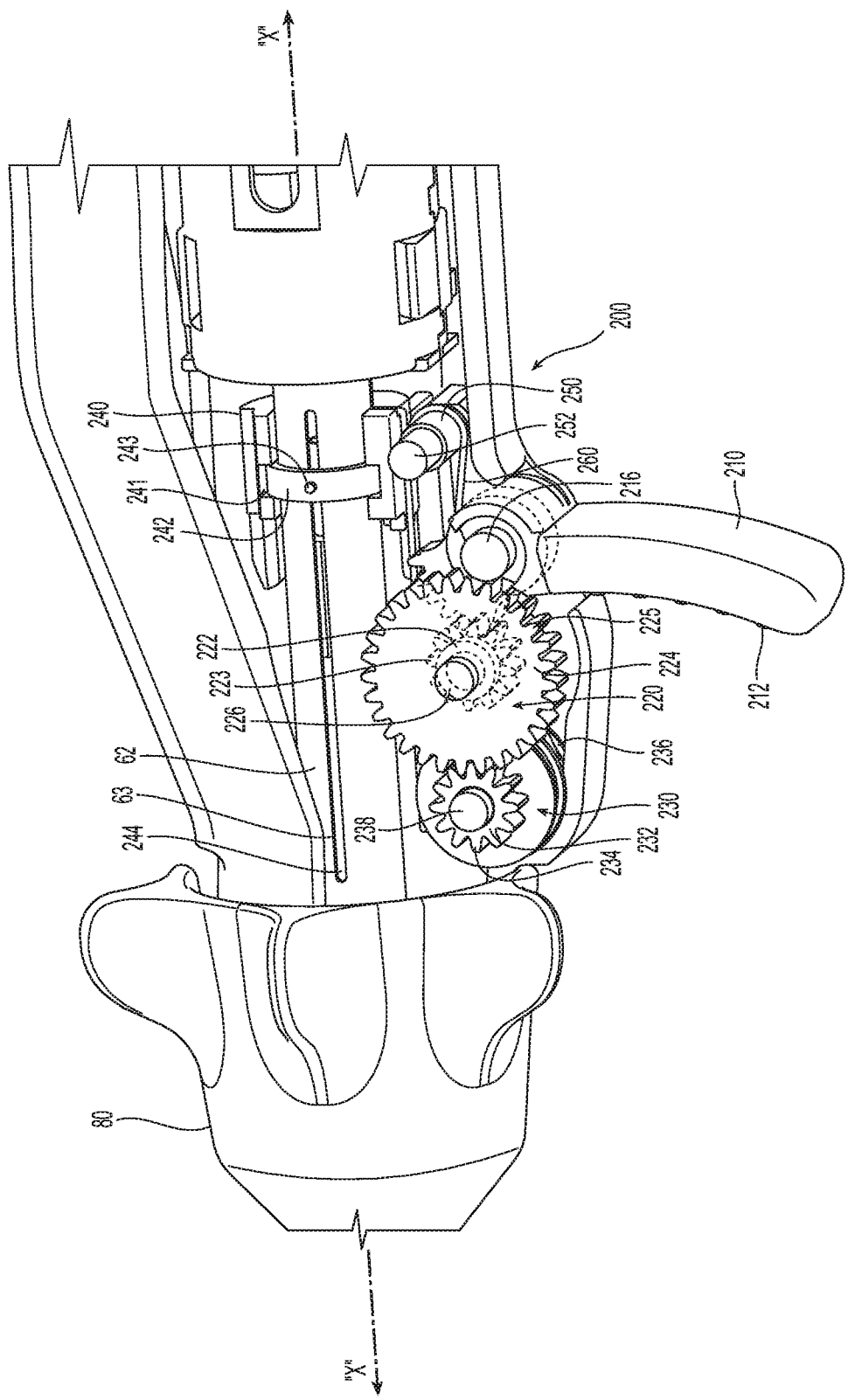

Further, and with continued reference to FIG. 16, knife slider 240 includes a cutout 241 that rotationally supports knife ring 242, such that knife ring 242 is rotatable about the longitudinal axis "X" with respect to knife slider 240 and with respect to trigger 210, for example. Additionally, knife ring 242 is pinned to a knife drive shaft 244 and to drive bar 62 by a ring pin 243, such that rotation of rotating assembly 80 causes rotation of drive bar 62 and knife ring 242 about the longitudinal axis "X" with respect to knife slider 240. Moreover, ring pin 243 extends through a longitudinal slot 63 of drive bar 62. Thus, longitudinal translation of knife slider 240 causes a corresponding longitudinal translation of knife ring 242 and knife drive shaft 244.

Accordingly, actuation of trigger 210 in a first direction (e.g., in the general direction of arrow "A") causes rotation of gear assembly 220, rotation of drive spool 230, movement of flexible drive member 260 around spool portion 236 of drive spool 230 and around roller 250, which causes distal translation or advancement of knife slider 240, knife ring 242 and knife drive shaft 244 to cut tissue, for example. Additionally, movement of trigger 210 in a second direction (e.g., in the general opposite direction of arrow "A") causes proximal translation or retraction of knife drive shaft 244.

Additionally, while the illustrated embodiments depict one type of surgical instrument (i.e., surgical forceps), the present disclosure includes the use of various features described herein in connection with other types of surgical devices including at least one pivotable handle or lever. For instance, various handle assemblies for actuating handle(s) and corresponding drive assemblies are contemplated for translating drive bar 62 and are discussed in commonly-owned U.S. Pat. No. 7,857,812, the entire contents of which are incorporated by reference herein.

Additionally, further details of a surgical forceps having a similar handle assembly to the disclosed handle assembly 30 are disclosed in U.S. Pat. No. 8,430,876, the entire contents of which being incorporated by reference herein. Further details of an electrosurgical instrument are disclosed in U.S. Pat. Nos. 7,101,371 and 7,083,618, the entire contents of which being incorporated by reference herein.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 17:
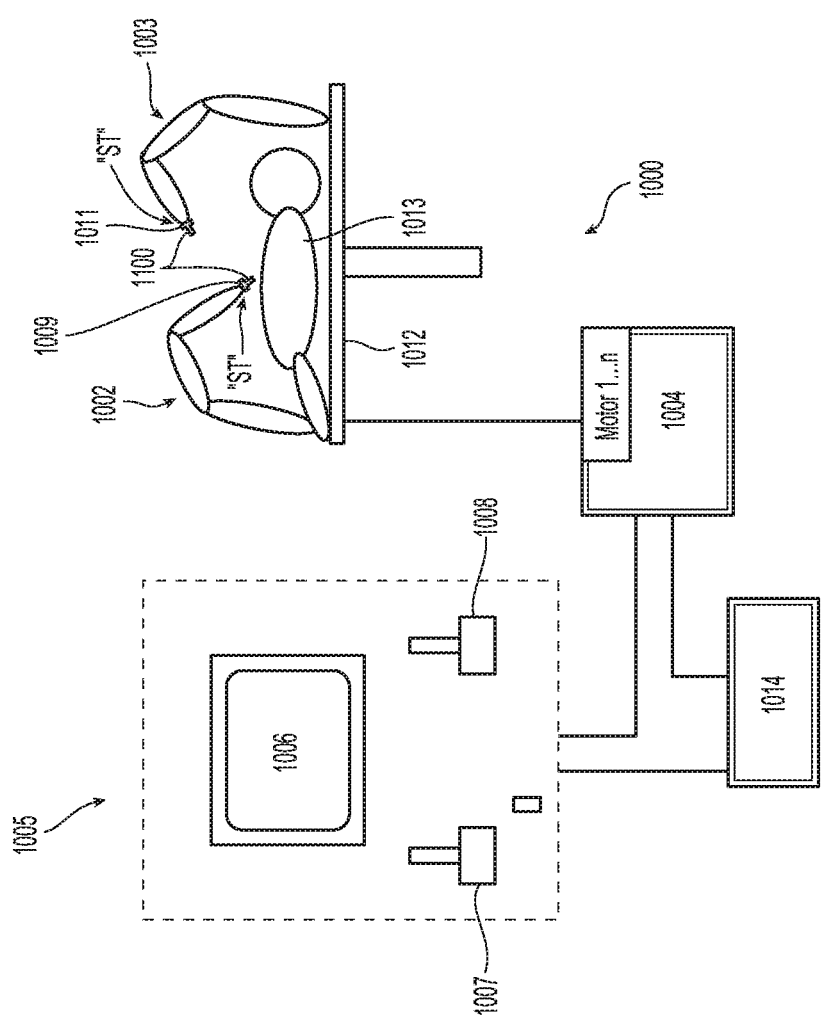
FIG. 17 is a schematic illustration of a surgical system in accordance with the present disclosure.

With particular reference to FIG. 17, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical instrument 10 (including end effector 300) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing;
   an elongated shaft extending distally from the housing and defining a longitudinal axis;
   an end effector assembly disposed adjacent a distal end of the elongated shaft, the end effector assembly including a first jaw member and a second jaw member, at least one of the jaw members movable with respect to the other jaw member from a spaced-apart position to a position closer to the other jaw member for grasping tissue; and a trigger assembly disposed in mechanical cooperation with the housing and configured to longitudinally translate a drive member, the trigger assembly including a trigger, a gear assembly, a spool, a slider, and a flexible drive member, the trigger disposed in mechanical cooperation with the gear assembly, the flexible drive member configured to engage the gear assembly, the spool, and the slider, the flexible drive member configured as a continuous loop, wherein movement of the trigger with respect to the housing results in movement of the flexible drive member with respect to the housing and longitudinal movement of the slider with respect to the housing.

2. The surgical instrument according to claim 1, further comprising a drive assembly disposed at least partially within the housing, the drive assembly including a drive bar extending at least partially through the elongated shaft such that longitudinal translation of the drive bar causes the jaw members to move between the spaced-apart position and the closer position for grasping tissue.

3. The surgical instrument according to claim 2, wherein the drive bar is rotatable about the longitudinal axis with respect to the housing.

4. The surgical instrument according to claim 2, wherein the drive bar is rotatable about the longitudinal axis with respect to the slider.

5. The surgical instrument according to claim 2, wherein the trigger assembly further comprises a ring rotationally supported by the slider.

6. The surgical instrument according to claim 5, wherein the ring is rotationally fixed with respect to the drive bar.

7. The surgical instrument according to claim 6, wherein the ring is longitudinally translatable with respect to the drive bar.

8. The surgical instrument according to claim 5, wherein the ring is rotatable relative to the housing.

9. The surgical instrument according to claim 5, wherein the slider is rotationally fixed relative to the housing.

10. The surgical instrument according to claim 2, wherein the drive member is longitudinally translatable with respect to the drive bar.

11. The surgical instrument according to claim 10, wherein the drive bar is rotatable with respect to the drive member.

12. The surgical instrument according to claim 1, wherein the gear assembly includes a first gear and a second gear, the first gear configured to engage the trigger, and the second gear configured to engage the spool.

13. A trigger assembly for use with a surgical instrument, the trigger assembly comprising:

a trigger;

a gear assembly disposed in mechanical cooperation with the trigger;

a spool;

a slider; and a flexible drive member, the flexible drive member configured to engage the gear assembly, the spool, and the slider, wherein actuation of the trigger results in movement of the flexible drive member with respect to the spool and longitudinal movement of the slider with respect to the spool, wherein an amount of contact between the flexible drive member and the spool remains constant during actuation of the trigger.

14. The trigger assembly according to claim 13, further comprising a ring rotationally supported by the slider.

15. The trigger assembly according to claim 14, wherein the ring is longitudinally translatable with respect to the spool.

16. The trigger assembly according to claim 13, wherein the gear assembly includes a first gear and a second gear, the first gear configured to engage the trigger, and the second gear configured to engage the spool.

17. The trigger assembly according to claim 16, wherein the first gear and the second gear are rotationally fixed with respect to each other.

18. The trigger assembly according to claim 13, wherein the flexible drive member is in contact with the spool and the slider.

19. The trigger assembly according to claim 13, wherein the spool includes a spool gear having a plurality of teeth configured to engage a portion of the gear assembly.

* * * * *